(12) United States Patent
Janik

(10) Patent No.: US 6,711,232 B1
(45) Date of Patent: Mar. 23, 2004

(54) X-RAY REFLECTIVITY MEASUREMENT

(75) Inventor: Gary R. Janik, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/414,905

(22) Filed: Apr. 16, 2003

(51) Int. Cl.[7] .............................................. G01N 23/20
(52) U.S. Cl. .......................................... 378/70; 378/86
(58) Field of Search ................................ 378/70, 86–89

(56) References Cited

U.S. PATENT DOCUMENTS

| 2,853,617 | A | 9/1958 | Berreman | 250/51 |
| 5,619,548 | A | 4/1997 | Koppel | 378/70 |
| 6,389,102 | B2 * | 5/2002 | Mazor et al. | 378/89 |
| 6,453,006 | B1 | 9/2002 | Koppel et al. | 378/86 |
| 6,507,634 | B1 | 1/2003 | Koppel et al. | 378/54 |
| 6,535,575 | B2 * | 3/2003 | Yokhin | 378/82 |

OTHER PUBLICATIONS

Naudon et al., *New Apparatus for Grazing X–ray Reflectometry in the Angle–Resolved Dispersive Mode*, J. Appl. Cryst., vol. 22, pp. 460–464, 1989.

* cited by examiner

*Primary Examiner*—Craig E Church
(74) *Attorney, Agent, or Firm*—Luedeka, Neely & Graham, P.C.

(57) ABSTRACT

An apparatus adapted for sensing characteristics of a layer disposed substantially within a plane, without making physical contact with the layer. An x-ray source produces x-rays, where the x-ray source has an axis disposed substantially perpendicular to the plane of the layer. An x-ray reflector has an axis disposed substantially perpendicular to the plane of the layer. The x-ray reflector receives the x-rays from the x-ray source and directs the x-rays received to a target spot on the layer at angles whereby the x-rays reflect off of the layer as reflected x-rays at a reflection angle. The reflected x-rays have properties that are indicative of the characteristics of the layer. A first x-ray blocking barrier is disposed substantially perpendicular to the plane of the layer, above the target spot. The first x-ray blocking barrier blocks at least a portion of the x-rays director toward and reflected off of the layer. The first x-ray blocking barrier and the layer define a gap, where the size of the gap determines at least in part a throughput and an angular resolution of the x-rays reflected off the layer. A receptor receives the reflected x-rays and produces signals based on the properties of the reflected x-rays. An analyzer receives the signals from the receptor and determines the characteristics of the layer based at least in part on the properties of the reflected x-rays.

20 Claims, 5 Drawing Sheets

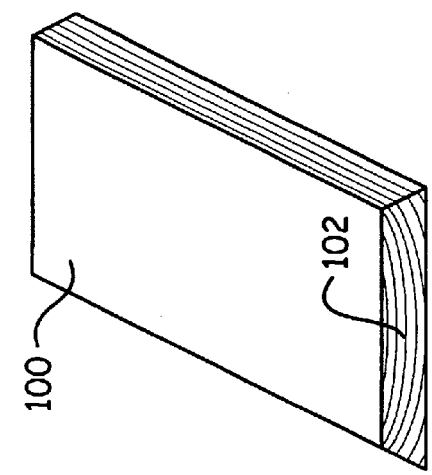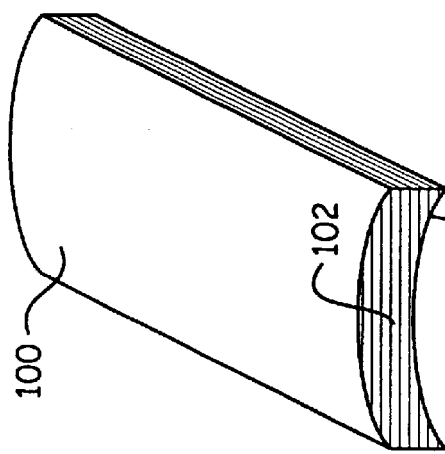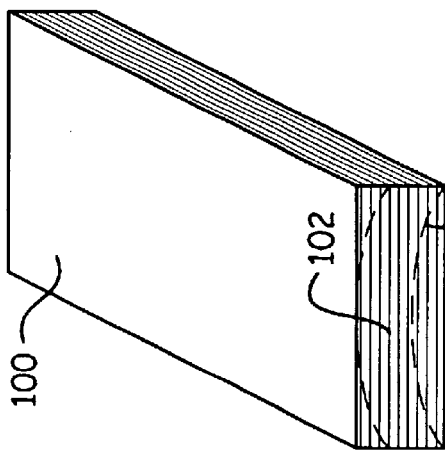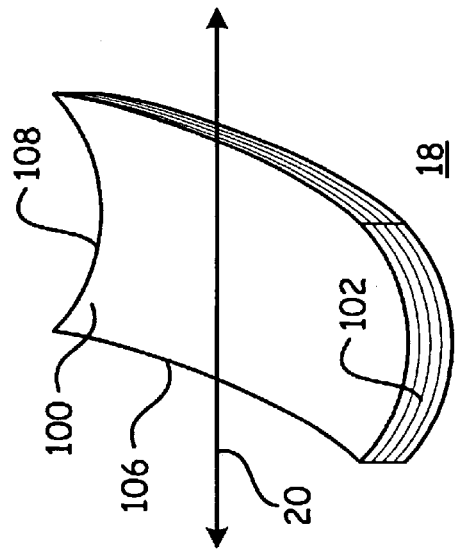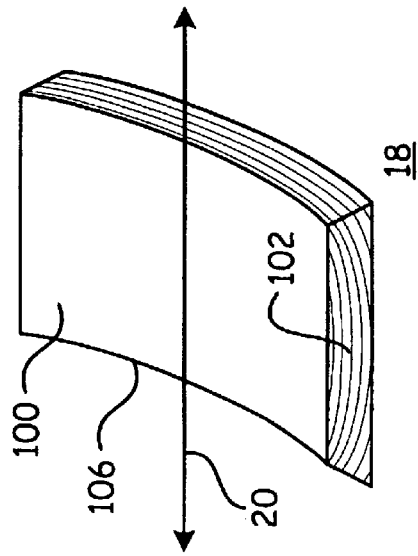

X-RAY REFLECTIVITY MEASUREMENT

FIELD

This invention relates to the field of instrumentation for measuring the physical properties of thin films, such as those used in the microelectronics industry. More particularly, this invention relates to the measurement of film topography and thickness using an x-ray reflectivity system.

BACKGROUND

X-ray reflectivity is a technology that can be used to determine physical properties of a layer on a substrate. For example, using x-ray reflectivity, the density, thickness, and surface roughness of a layer can be determined. Such information tends to be very useful in some industries, such as in the microelectronics industry, where the proper formation of various layers and the close control of the processes by which they are made are vital to successful fabrication of the devices in which the layers are formed.

X-ray reflectivity measurements are made by directing an x-ray beam toward the layer at an incident angle. As the x-rays reflect off of the layer, they are received by a detector of some type, such as a scintillation screen. The angles at which the x-rays reflect off of the layer, and the intensity of the reflected rays at those different angles, contains information about the physical properties of the layer, such as the thickness, roughness, and density, as mentioned above.

There are several parameters in regard to the construction and operation of an x-ray reflectometer that are important in order to get accurate results. One parameter is the x-ray throughput of the x-ray reflectometer. In other words, the x-ray reflectometer must be constructed so that a sufficient number of x-rays reflect off of the sample and are received by the detector, or the detector is unable to produce strong enough signals for a valid reading. Another important parameter is the angular resolution of the x-ray reflectometer. Angular resolution is the degree to which the x-rays that reflect off of the surface of the layer at different angles are separated across the detector. In other words, if two reflected beams having different reflectance angles are read as having the same reflectance angle by the detector, because for example they are so close together that the detector cannot resolve the angular difference between them, then an inaccurate result will be reported by the reflectometer.

Some applications are relatively tolerant as to a reduced x-ray throughput, and other applications are relatively tolerant as to a reduced angular resolution. Ideally, it would be beneficial to be able to adjust x-ray throughput and angular resolution as desired. Unfortunately, the layout of x-ray reflectometers tends to make it extremely difficult to adjust either of these two parameters.

There is a need, therefore, for an improved x-ray reflectometer design that, for example, enables angular resolution and x-ray throughput to be more easily adjusted.

SUMMARY

The above and other needs are met by an apparatus adapted for sensing characteristics of a layer disposed substantially within a plane, without making physical contact with the layer. An x-ray source produces x-rays, where the x-ray source has an axis disposed substantially perpendicular to the plane of the layer. A curved x-ray is reflector has an axis disposed substantially perpendicular to the plane of the layer. The x-ray reflector receives the x-rays from the x-ray source and directs the x-rays received to a target spot on the layer at angles whereby the x-rays reflect off of the layer as reflected x-rays at a reflection angle. The reflected x-rays have properties that are indicative of the characteristics of the layer.

A first x-ray blocking barrier is disposed substantially perpendicular to the plane of the layer, above the target spot. The first x-ray blocking barrier blocks at least a portion of the x-rays directed toward and reflected off of the layer. The first x-ray blocking barrier and the layer define a gap, where the size of the gap determines at least in part a throughput and an angular resolution of the x-rays reflected off the layer. A receptor receives the reflected x-rays and produces signals based on the properties of the reflected x-rays. An analyzer receives the signals from the receptor and determines the characteristics of the layer based at least in part on the properties of the reflected x-rays.

In this manner, the angular resolution can be increased by reducing the size of the gap, or alternately, the x-ray throughput can be increased by increasing the size of the gap. Thus, control over the characteristics of the system is available through adjusting the gap. This is made possible in part because the x-ray source and the x-ray reflector have an orientation relative to the layer that is different from that of prior art x-ray systems.

In various preferred embodiments, a second x-ray blocking barrier is disposed substantially perpendicular to the plane of the layer, between the x-ray reflector and the layer. The second x-ray blocking barrier blocks at least a portion of any x-rays that are not directed to the target spot on the layer. Preferably, the x-ray reflector is comprised of at least one of silicon, germanium, and lithium fluoride, and most preferably is formed of a single crystal structure, where a crystal plane of the single crystal structure has a curvature defined along the axis of the x-ray reflector and the crystal plane of the single crystal structure also has a curvature defined around the axis of the x-ray reflector.

Preferably, a surface of the single crystal structure of the x-ray reflector has a cylindrical curvature defined around the axis of the x-ray reflector. In one embodiment, the x-ray reflector is formed of a single crystal structure, where a surface of the single crystal structure has an elliptical curvature defined both around and along the axis of the x-ray reflector. The receptor is preferably a charge coupled device array. The x-ray source preferably produces a divergent cone of x-rays directed toward the x-ray reflector, which in turn produces a convergent cone of x-rays substantially focused on the target spot of the layer. Most preferably the x-ray source is a linear focus x-ray tube.

In an alternate embodiment, the x-ray reflector is a Johnson geometry crystal. The size of the gap is preferably adjustable from about ten microns to about one hundred microns. A movable stage preferably selectively raises and lowers the layer relative to the first x-ray blocking barrier, and thereby adjusts the size of the gap. A sensor preferably determines the size of the gap. In a most preferred embodiment, the linear focus x-ray tube produces copper Ka x-rays from a source having dimensions of about twelve millimeters by about forty microns, and the spot on the layer is about forty microns in width.

In one embodiment the apparatus includes a second x-ray source having an axis and disposed above the linear focus x-ray tube. The axis of the second x-ray source is substantially parallel to the axis of the linear focus x-ray tube. A second x-ray reflector with an axis is disposed above the x-ray reflector. The axis of the second x-ray reflector is substantially parallel to the axis of the x-ray reflector. The second x-ray source and the second x-ray reflector increase the range of reflection angles measured by the charge coupled device array receptor, and thus increase the angular resolution of the apparatus.

In an alternate embodiment, the apparatus includes a second x-ray source with an axis, disposed beside the linear focus x-ray tube. The axis of the second x-ray source is substantially parallel to the axis of the linear focus x-ray tube. A second x-ray reflector with an axis is disposed beside the x-ray reflector. The axis of the second x-ray reflector is substantially parallel to the axis of the x-ray reflector. The second x-ray source and the second x-ray reflector increase the x-ray throughput.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein:

FIG. 5 is a perspective view planar crystal, FIG. 6 is a perspective view of the crystal of FIG. 5 that has been cut to a radius, FIG. 7 is a perspective view of the crystal of FIG. 6 that has been flattened, FIG. 8 is a perspective view of the crystal of FIG. 7 that has been curved around its axis, and FIG. 9 is a perspective view of a toroidal shaped crystal that has been bent both along and around its axis.

DETAILED DESCRIPTION

Figure 1:
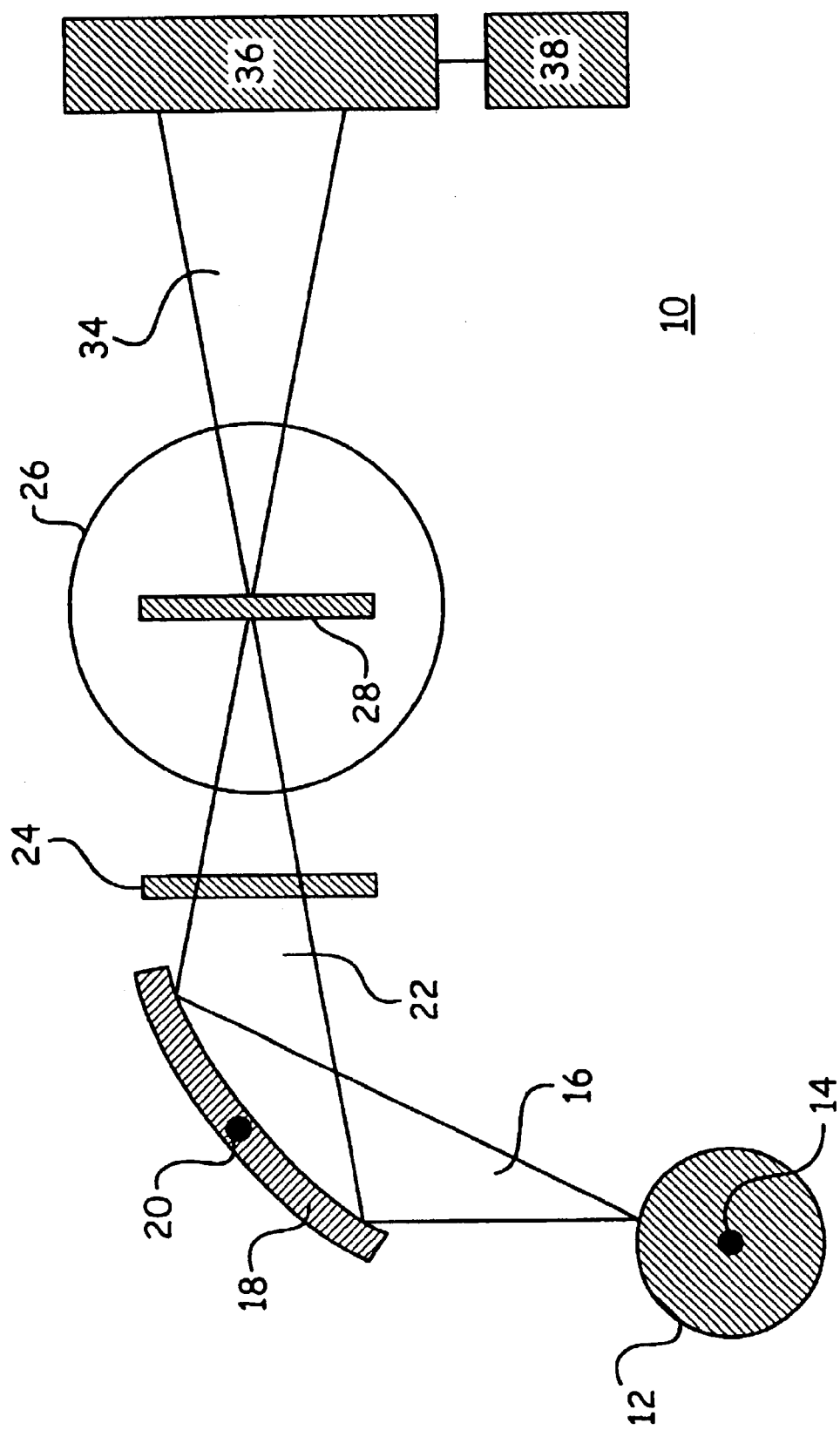
FIG. 1 is a top plan view functional block diagram of a first embodiment of an x-ray system according to the present invention.

With reference now to FIG. 1, there is depicted a top plan view of a functional block diagram of an x-ray system 10 according to the present invention. X-rays 16 are produced by an x-ray source 12, which is preferably a linear focus x-ray tube. The x-rays 16 are preferably copper Kα x-rays. The linear focus of the electron beam in the x-ray source 12 is preferably about twelve millimeters by about forty microns, and aligned lengthwise along the axis 14. The x-ray source 12 preferably produces a divergent cone of x-rays 16 that are directed toward a reflector 18. The divergent cone of x-rays 16 is wide enough as to utilize a substantial portion of the focusing surface area of the reflector 18.

The x-ray source 12 has an axis 14, which is preferably the focus axis, which in FIG. 1 is disposed at an angle that is substantially perpendicular to the plane of the paper on which the figure is printed. This axis 14 is disposed in reference to a sample 26, such as an integrated circuit substrate, on which it is desired to take readings. The sample 26 is disposed substantially within a plane, which in FIG. 1 is coplanar with the paper on which the figure is printed. The reflector 18 also has an axis 20, which is substantially parallel to the axis 14 of the x-ray source 12, and is thus substantially perpendicular to the plane of the sample 26.

With the axis 14 of the x-ray source 12 and the axis 20 of the reflector 18 disposed perpendicularly to the plane of the sample 26, the system 10 has a different configuration than prior art reflectometers. Prior art reflectometers tend to be more vertically oriented, instead of the substantially horizontal orientation as depicted in FIG. 1.

For example, prior art reflectometers tend to place an x-ray source either above or below the sample 26, with the axis of the x-ray source substantially parallel to the plane of the sample 26. Further, prior art reflectometers also tend to place the axis of the reflector parallel to the plane of the sample 26. Thus, the configuration of the system 10 as described herein is quite different from these prior art designs, which new design yields benefits as described hereafter.

Figure 2:
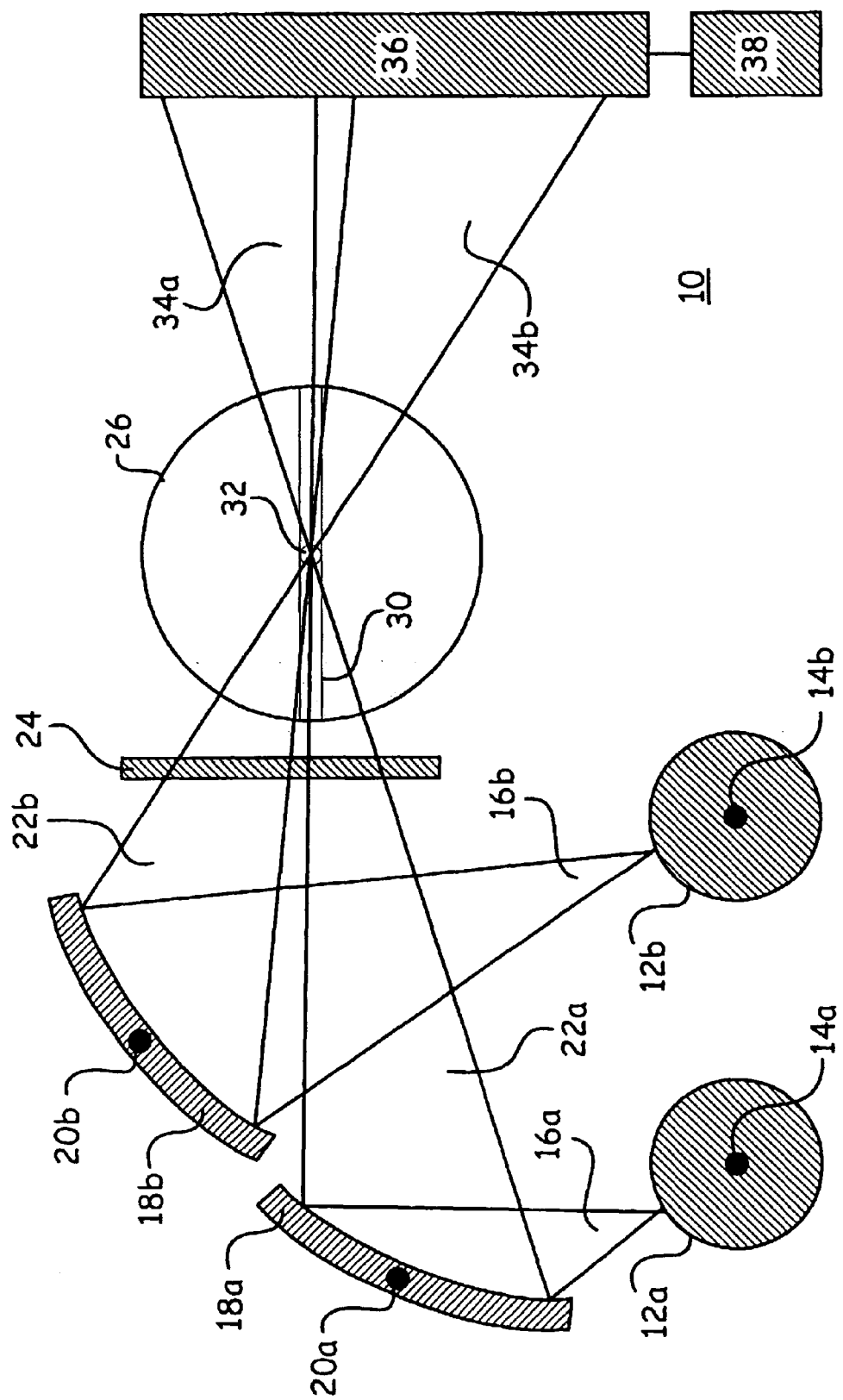
FIG. 2 is a top plan view functional block diagram of a second embodiment of an x-ray system according to the present invention.
Figure 3:
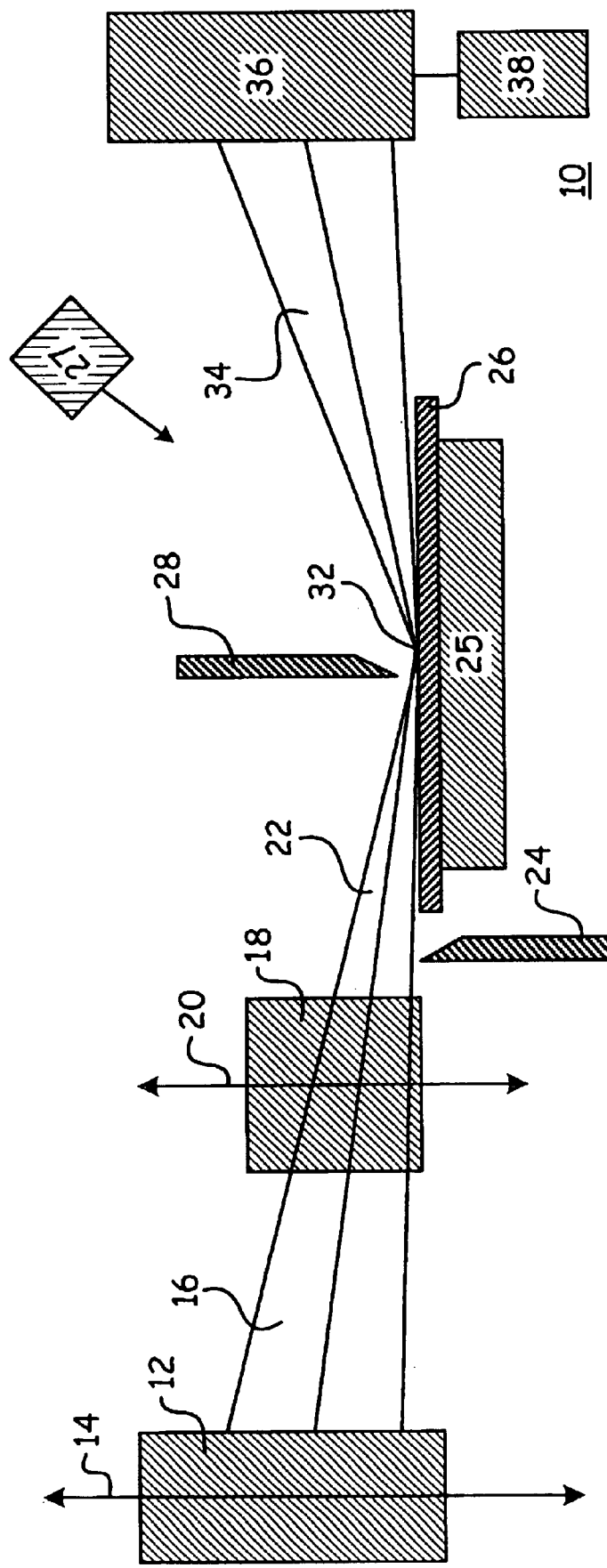
FIG. 3 is a side view functional block diagram of the first embodiment of an x-ray system according to the present invention.

The x-ray reflector 18 is preferably formed of a single crystal of a material suitably for receiving and reflecting x-rays, such as silicon, germanium, and lithium fluoride. The x-ray reflector 18 is configured so as to receive the divergent cone of x-rays 16 and produce a convergent cone of x-rays 22, which is most preferably directed toward a target spot 32 on the sample 26, as depicted in FIG. 2. Thus, the reflector 18 preferably acts a monochromator. The spot 32 on the sample 26 is preferably no more than about eighty microns in width, so that it fits within a standard 80–100 micron wide scribe line 30 on the sample 26, also depicted in FIG. 2. In this manner, readings can be taken on a layer on the sample 26 in a scribe line 30 of the sample 26, such as is commonly found on a substrate on which integrated circuits are formed.

In some embodiments the reflector 18 is flat. However, in more preferred embodiments, at least the crystal plane of the reflector 18 is curved in some manner, and the surface of the reflector 18 may also be curved in some manner. For example, the crystal plane of the reflector 18 may be curved around the axis 20, which means that it is curved in the manner that the surface of the reflector 18 is curved as depicted in FIG. 1, or the crystal plane of the reflector 18 may be curved along the axis 20, which is a curvature that is rotated ninety degrees from the curvature of the surface of the reflector 18 as depicted in FIG. 1. Further, the crystal plane of the reflector 18 may be curved both along and around the axis 18, which is the most preferred embodiment.

However, crystal plane curvature along or around the axis 20 does not necessarily indicate that the surface of the reflector 18 is also curved along or around the axis 20. It is possible to curve the crystal plane without curving the surface of the reflector 18, as describe in more detail below. In a most preferred embodiment, the crystal plane of the reflector 18 is curved both along and around the axis 20, but the surface of the reflector 18 is only curved around the axis 20, as depicted in FIG. 1. Most preferably, the curvature of the surface of the reflector 18 is cylindrical and the reflector 18 is symmetrically cut. However, in other embodiments the curvature of the surface of the reflector 18 may be elliptical, or have some other shape. Further, the surface may be curved along the axis 20 but not around the axis 20, or may be curved both along and around the axis 20.

By having the crystal plane of the reflector 18 bent in two directions, both around and along the axis 20, but the surface of the reflector 18 bent in only one direction, around the axis 20, the reflector is able to be formed to a larger size than if the surface was bent in two directions, because the stress on the crystal plane is not as great as it would be if the surface was bent in two directions. In addition, the reflector tends to be more easily fabricated in this preferred configuration. By having a larger reflector 18, the x-ray throughput of the system 10 can be increased, because there is a larger surface on which to receive the divergent cone of x-rays 12 and from which to focus the convergent cone of x-rays 22.

The reflector 18 is most preferably formed according the method as described in conjunction with FIGS. 5–8. A slab 100 of the crystalline material is formed, with the crystal structure 102 formed in a substantially planar orientation with the surface of the slab 100, as depicted in FIG. 5. A desired curvature 104 of the crystal plane is identified, and the surface of the slab 100 is cut or ground to the desired curvature 104, as depicted in FIG. 6. As seen in FIG. 6, the orientation of the crystal structure 102 is at this point no longer planar with the surface of the slab 100.

The slab 100 is next flattened out as depicted in FIG. 7, so that the surfaces of the slab 100 are again planar. However, in so doing, the crystal structure 102 has been bent or curved in one direction, as is represented in FIG. 7. Then, as depicted in FIG. 8, the slab 100 is bent to give it a curve 106 around the axis 20, which also bends the crystal plane around the axis 20. Thus, in the embodiment depicted in FIG. 8, the crystal plane 102 is bent both around and along the axis 20, while the surface of the slab 100 is bent only around the axis 20, which bend 106 may be either cylindrical, elliptical, or some other shape of bend.

In an alternate embodiment depicted in FIG. 9, the slab 100, as initially depicted in FIG. 5, is not cut or ground as depicted in FIG. 6, but rather is bent to a curve 106 around the axis 20, and is also bent to a curve 108 along the axis 20. Thus, in the embodiment depicted in FIG. 9, the crystal plane 102 of the slab 100 is curved both around and along the axis 20, while the surface of the slab 100 is also curved both around and along the axis 20, in a shape that may be either cylindrical or elliptical in either direction.

The x-ray reflector 18 may also be a Johansson geometry crystal, in which the slab 100 is ground such that the crystal plane is bent to a radius of 2R around the axis 20 while the surface of the x-ray reflector 18 is bent to a radius of R around the axis 20, so that all of the points of reflection of the reflector 18 lie on what is called the Rowland circle. In this manner, the x-rays 16 from the x-ray source 12 can be director across a relatively larger portion of the reflector 18, and the reflector 18 is able to then direct all of those x-rays 22 towards a very small diameter target spot 32 on the sample 26. Thus, the Johansson geometry crystal makes very efficient use of the x-rays 16 produced by the x-ray source 12. In a preferred embodiment, the x-ray reflector 18 has a focal length of about eighty millimeters, with an effective working distance of about one hundred and sixty millimeters between the x-ray source 12 and the target spot 32 on the sample 26.

A second x-ray blocking barrier 24 is preferably disposed along the path of the convergent cone of x-rays 22 between the reflector 18 and the sample 26. The second x-ray blocking barrier 24 is preferably placed with a top surface of the barrier disposed very near the level of the top surface of the sample 26, and perpendicular to the plane of the sample 26, as depicted in FIG. 2. As x-rays are penetrating wavelengths, the second x-ray blocking barrier 24 preferably substantially prohibits any errantly directed x-rays from passing from the direction of the x-ray source 12 and the reflector 18 toward the sample 26 along any other path except the intended divergent cone of x-rays 22. The second x-ray blocking barrier 24 is preferably formed of an x-ray absorbing material, such as tungsten. The upper edge of the second x-ray blocking barrier 24 is preferably tapered.

As mentioned above, the reflector 18 preferably directs a convergent cone of x-rays 22 toward a target spot 32 on the sample 26. The sample 26 includes one or more layers, on which it is desired to take readings. The x-rays 22 are received by the layer at angles whereby they reflect off of the layer as reflected x-rays 34 having reflection angles. The reflected x-rays 34 have properties that are indicative of the characteristics of the layer on the sample 26. For example, the angles at which the x-rays 34 are reflected, and the intensity of the x-rays 34 at the various reflection angles are properties of the x-rays 34 that have information in regard to the surface roughness, thickness, and density of various layers on the sample 26. Thus, the system 10 senses various characteristics of the layer without making physical contact with the layer.

A first x-ray blocking barrier 28 is preferably disposed over the sample 26 in the vicinity of the target spot 32. The first x-ray blocking barrier 28 is not depicted in FIG. 2, so that the target spot 32 and the scribe line 30 of the sample 26 may be more easily seen. However, the first x-ray blocking barrier 28 is preferably included in all embodiments of the present invention. The first x-ray blocking barrier 28 is preferably formed of a material that absorbs x-rays, such as tungsten, and is preferably disposed in a perpendicular orientation relative to the plane of the sample 26. The first x-ray blocking barrier 28 preferably defines a gap between the bottom edge of the first x-ray blocking barrier 28, which is most preferably tapered, and the upper surface of the sample 26.

In a most preferred embodiment, the gap is adjustable as to size by at least one of raising and lowering the sample 26, such as with the movable stage 25, or raising and lowering the first x-ray blocking barrier 28. A sensor 27 preferably determines the size of the gap so that it is known, and so that the first x-ray blocking barrier 28 does not hit the sample 26. The sensor 27 may either directly measure the size of the gap, or may infer the size of the gap based on the position of at least one of the first x-ray blocking barrier 28 and the stage 25. The sensor 27 may be configured as one or more of an optical sensor, pressure sensor, or electromagnetic sensor.

The first x-ray blocking barrier 28 is preferably adapted to selectively block a portion of the x-rays 22 directed toward the sample 26, and may alternately or additionally block a portion of the x-rays 34 reflected from the sample 26. Thus, by increasing the size of the gap the x-ray throughput of the system 10 is increased, and by decreasing the size of the gap the x-ray throughput of the system 10 is decreased. While the benefits of having an increased x-ray throughput have been briefly described above, the benefits of decreasing the x-ray throughput in this manner is described hereafter.

The reflected x-rays 34 are preferably received by a receptor 36, which is most preferably a charge coupled device array. Thus, the receptor 36 is able to sense both where the reflected x-rays 34 impinge upon it, and the intensity with which the reflected x-rays 34 impinge. The receptor 36 is preferably in communication with an analyzer 38, which receives the angular and intensity information from the receptor 36 in the form of signals from the receptor 36, and determines the characteristics of the layer on the sample 26 as desired. Thus, the characteristics of the layer on the sample 26 are determined based at least in part on the properties of the reflected x-rays 34.

As mentioned above, increasing the gap increases x-ray throughput, and decreasing the gap decreases x-ray throughput. However, increasing the gap in the system 10 of the current invention also decreases angular resolution, and decreasing the gap increases angular resolution. Therefore, in the system 10 according to the present invention, x-ray throughput can be increased by selectively trading off angular resolution, and angular resolution can be increased by selectively trading off x-ray throughput. Thus, the adjustment of the gap can be used to optimize measurements of different film thicknesses and characteristics.

Without being bound by theory, the angular resolution is determined by taking the arctangent of the ratio of the pixel size on the detector 36, which is most preferably about twenty microns, to the distance between the detector 36 and the target spot 32, which is most preferably about three hundred and ten millimeters. This yields an initial fixed angular resolution with a value of about 0.0037 degrees. Of course, this angular resolution can be adjusted by moving the detector 36 either closer to the target spot 32, thereby increasing the value of the angular resolution, or by moving the detector 36 farther from the target spot 32, thereby decreasing the value of the angular resolution. It is appreciated that larger angular resolution values indicate a reduced degree of angular resolution, or in other words a reduced ability to resolve differences between angles, and a smaller angular resolution value indicates an increased degree of angular resolution, or in other words an increased ability to resolve differences between angles.

The size of the gap, which controls the solid angle of the x-rays 22 which can reach the target spot 32, and either additionally or alternately controls the solid angle of the x-rays 34 that are reflected off of the target spot 32, additionally impacts the angular resolution. The degree by which the gap affects angular resolution is determined by taking the arctangent of the ratio of twice the gap size by the distance between the detector 36 and the target spot 32. For example, with a gap size of about ten microns, and a detector distance of about three hundred and ten millimeters, the effective value of the angular resolution is increased by about 0.0037 degrees to a total of about 0.0074 degrees.

However, by increasing the gap to about one hundred microns, the effective value of the angular resolution is increased by about 0.037 degrees to a total of about 0.0407 degrees. Thus, by increasing the size of the gap the ability of the system to discern differences in reflectance angle has been decreased, or in other words angular resolution has been decreased, but x-ray throughput has been increased. In the example given, the decrease in angular resolution has been traded off for about a ten-fold increase in x-ray throughput, as the gap was increased from about ten microns to about one hundred microns.

As a specific example, the system 10 can be used such as to investigate a patterned semiconductor wafer with a fifty angstrom thick tantalum nitride barrier film under a fifteen hundred angstrom thick copper seed layer. The size of the gap is adjusted to be about ten microns, and the shutter on the x-ray source 12 is opened for about five seconds and then closed again. The charges on the charge coupled device array 36 are read out, and a high resolution measurement is taken of the copper seed layer. The gap is then adjusted to about one hundred microns. The shutter on the x-ray source 12 is again opened for about ten seconds, and then closed. The charge on the receptor 36 is again read out, and a low resolution measurement of the thin tantalum nitride barrier layer is taken. The low resolution measurement on the tantalum nitride barrier layer is adequate since the barrier fringes are very widely spaced in angle.

Thus, the present system 10 as described can measure transparent and opaque films having a thickness of between about ten angstroms and about two thousand angstroms on patterned wafers with acceptable throughput. The system 10 is especially well adapted for measuring copper seed and tantalum barrier layers, high k gates with metal contact layers, silicon-germanium films, and silicon dioxide, silicon nitride, silicon dioxide stacks. The system 10 could also be configured as part of a small angle x-ray scattering system (SAXS). As described, the system 10 is relatively easily fabricated, reduces spot size on the sample 26, and tailors angular resolution and x-ray throughput.

Figure 4:
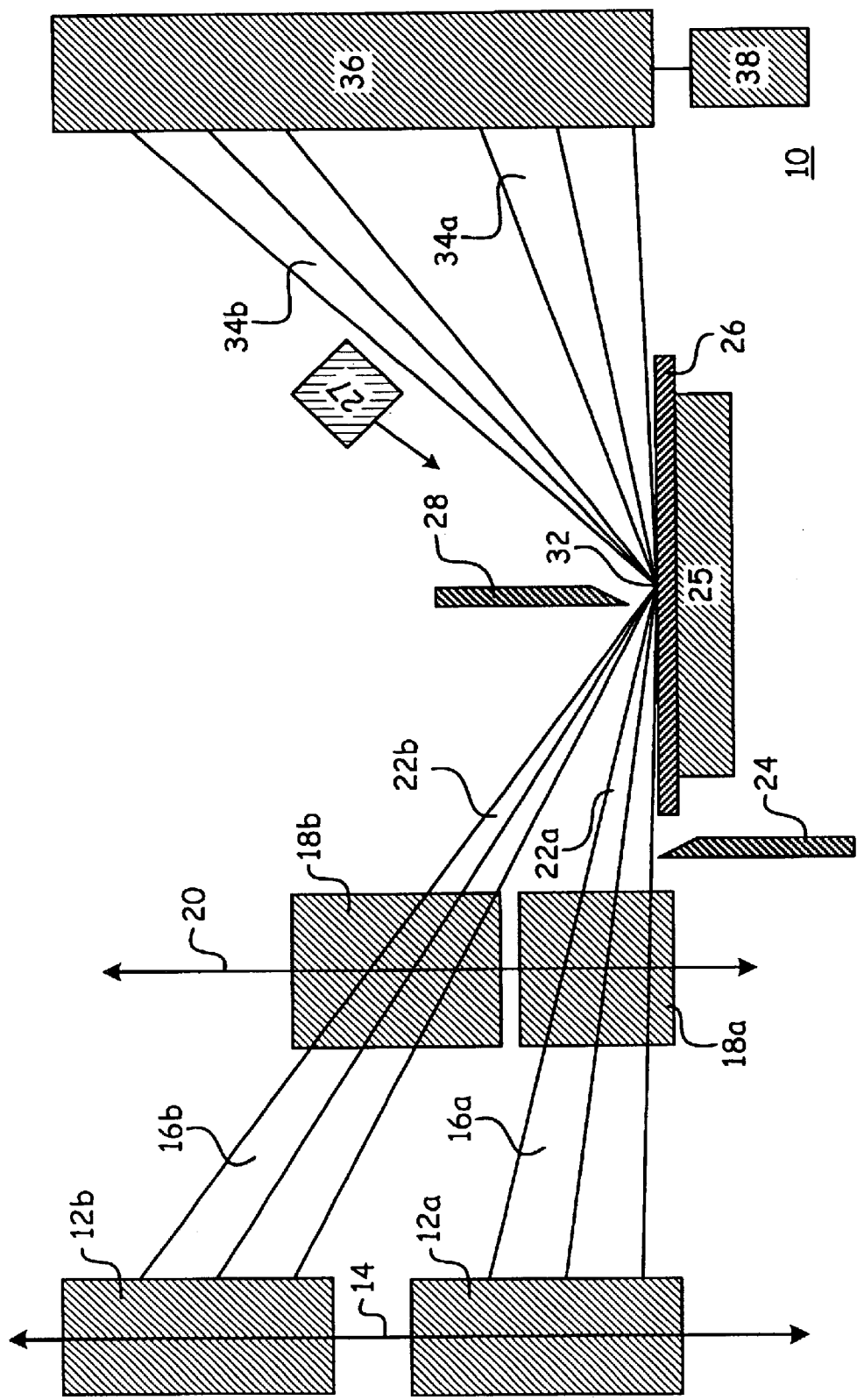
FIG. 4 is a side view functional block diagram of a third embodiment of an x-ray system according to the present invention.

FIGS. 2 and 4 depict alternate embodiments of the system 10. In FIG. 2, the system has more than one x-ray source 12a and 12b, and more than one reflector 18a and 18b. As depicted in FIG. 2, the axes 14a and 14b of the x-ray sources 12a and 12b are substantially parallel one to another, and the x-ray sources 12a and 12b are disposed beside each other. Similarly, the axes 20a and 20b of the reflectors 18a and 18b are substantially parallel one to another, and the reflectors 18a and 18b are disposed beside each other. With this configuration of the system 10, the x-ray throughput is increased over a single x-ray beam system.

In FIG. 4, the system 10 again has more than one x-ray source 12a and 12b, and more than one reflector 18a and 18b. As depicted in FIG. 4, the axes 14a and 14b of the x-ray sources 12a and 12b are substantially parallel one to another, however, the x-ray sources 12a and 12b are disposed above and below each other. Similarly, the axes 20a and 20b of the reflectors 18a and 18b are substantially parallel one to another, but the reflectors 18a and 18b are disposed above and below each other. With this configuration of the system 10, the range of reflection angles measured by the detector 26 is increased over a single x-ray beam system.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as is suited to the particular use contemplated. All such modifications and variations are within the scope of the invention as determined by the appended claims when interpreted in accordance with the breadth to which they are fairly, legally, and equitably entitled.

What is claimed is:

1. An apparatus adapted for sensing characteristics of a layer disposed substantially within a plane, without making physical contact with the layer, the apparatus comprising:

an x-ray source adapted for producing x-rays, the x-ray source having an axis, the axis of the x-ray source disposed substantially perpendicular to the plane of the layer, an x-ray reflector having an axis, the axis of the x-ray reflector disposed substantially perpendicular to the plane of the layer, the x-ray reflector adapted for receiving the x-rays from the x-ray source and directing the x-rays received to a target spot on the layer at angles whereby the x-rays reflect off of the layer as reflected x-rays at a reflection angle, where the reflected x-rays have properties that are indicative of the characteristics of the layer, a first x-ray blocking barrier disposed substantially perpendicular to the plane of the layer, the first x-ray blocking barrier further disposed above the target spot on the layer, the first x-ray blocking barrier adapted for blocking at least a portion of the x-rays director toward and reflected off of the layer, the first x-ray blocking barrier and the layer defining a gap, where a size of the gap determines at least in part a throughput and an angular resolution of the x-rays reflected off the layer, a receptor adapted for receiving the reflected x-rays and producing signals based on the properties of the reflected x-rays, and an analyzer adapted for receiving the signals from the receptor and determining the characteristics of the layer based at least in part on the properties of the reflected x-rays.

2. The apparatus of claim 1, further comprising a second x-ray blocking barrier disposed substantially perpendicular to the plane of the layer, the second x-ray blocking barrier disposed between the x-ray reflector and the layer, the second x-ray blocking barrier adapted for blocking at least a portion of any x-rays that are not directed to the target spot on the layer.

3. The apparatus of claim 1, wherein the x-ray reflector is comprised of at least one of silicon, germanium, and lithium fluoride.

4. The apparatus of claim 1, wherein the x-ray reflector is formed of a single crystal structure, where a crystal plane of the single crystal structure has a curvature defined along the axis of the x-ray reflector and the crystal plane of the single crystal structure also has a curvature defined around the axis of the x-ray reflector.

5. The apparatus of claim 1, wherein the x-ray reflector is formed of a single crystal structure, where a surface of the single crystal structure has a cylindrical curvature defined around the axis of the x-ray reflector.

6. The apparatus of claim 1, wherein the x-ray reflector is formed of a single crystal structure, where a surface of the single crystal structure has an elliptical curvature defined both around and along the axis of the x-ray reflector.

7. The apparatus of claim 1, wherein the receptor is a charge coupled device array.

8. The apparatus of claim 1, wherein the x-ray source produces a divergent cone of x-rays directed toward the x-ray reflector, and the x-ray reflector produces a convergent cone of x-rays substantially focused on the target spot of the layer.

9. The apparatus of claim 1, wherein the x-ray source is a linear focus x-ray tube.

10. An apparatus adapted for sensing characteristics of a layer disposed substantially within a plane, without making physical contact with the layer, the apparatus comprising:

a linear focus x-ray tube adapted for producing x-rays, the linear focus x-ray tube having an axis, the axis of the linear focus x-ray tube disposed substantially perpendicular to the plane of the layer, an x-ray reflector having an axis, the axis of the x-ray reflector disposed substantially perpendicular to the plane of the layer, the x-ray reflector formed of a single crystal structure having a crystal plane bent in a first direction along the axis and in a second direction around the axis, and a surface bent in the second direction around the axis, the x-ray reflector adapted for receiving the x-rays from the linear focus x-ray tube and directing the x-rays received to a target spot on the layer at angles whereby the x-rays reflect off of the layer as reflected x-rays at a reflection angle, where the reflected x-rays have properties that are indicative of the characteristics of the layer, a first x-ray blocking barrier disposed substantially perpendicular to the plane of the layer, the first x-ray blocking barrier further disposed above the target spot on the layer, the first x-ray blocking barrier adapted for blocking at least a portion of the x-rays director toward and reflected off of the layer, the first x-ray blocking barrier and the layer defining a gap, where a size of the gap determines at least in part both a throughput and an angular resolution of the x-rays reflected off the layer, where the gap is adjustable through a range, a second x-ray blocking barrier disposed substantially perpendicular to the plane of the layer, the second x-ray blocking barrier disposed between the x-ray reflector and the layer, the second x-ray blocking barrier adapted for blocking at least a portion of any x-rays that are not directed to the target spot on the layer, a charge coupled device array receptor adapted for receiving the reflected x-rays and producing signals based on the properties of the reflected x-rays, including an intensity of the reflected x-rays as a function of angle of the reflected x-rays, and an analyzer adapted for receiving the signals from the receptor and determining the characteristics of the layer based at least in part on the properties of the reflected x-rays.

11. The apparatus of claim 10, wherein the x-ray reflector is comprised of at least one of silicon, germanium, and lithium fluoride.

12. The apparatus of claim 1, wherein the x-ray reflector is a Johansson geometry crystal.

13. The apparatus of claim 10, wherein the size of the gap is adjustable from about ten microns to about one hundred microns.

14. The apparatus of claim 10, further comprising a movable stage adapted to selectively raise and lower the layer relative to the first x-ray blocking barrier, and thereby adjust the size of the gap.

15. The apparatus of claim 10, further comprising a sensor adapted to determine the size of the gap.

16. The apparatus of claim 10, wherein the linear focus x-ray tube produces copper x-rays.

17. The apparatus of claim 10, wherein the spot on the layer is less than about one hundred microns in width.

18. The apparatus of claim 10, further comprising:

a second x-ray source having an axis, the second x-ray source disposed above the linear focus x-ray tube, the axis of the second x-ray source substantially parallel to the axis of the linear focus x-ray tube, a second x-ray reflector having an axis, the second x-ray reflector disposed above the x-ray reflector, the axis of the second x-ray reflector substantially parallel to the axis of the x-ray reflector, and the second x-ray source and the second x-ray reflector adapted for increasing a range of reflection angles measured by the charge coupled device array receptor.

19. The apparatus of claim 10, further comprising:

a second x-ray source having an axis, the second x-ray source disposed beside the linear focus x-ray tube, the axis of the second x-ray source substantially parallel to the axis of the linear focus x-ray tube, a second x-ray reflector having an axis, the second x-ray reflector disposed beside the x-ray reflector, the axis of the second x-ray reflector substantially parallel to the axis of the x-ray reflector, and the second x-ray source and the second x-ray reflector adapted for increasing the x-ray throughput.

20. An apparatus adapted for sensing characteristics of a layer disposed substantially within a plane, without making physical contact with the layer, the apparatus comprising:

a linear focus x-ray tube adapted for producing x-rays, the linear focus x-ray tube having an axis, the axis of the linear focus x-ray tube disposed substantially perpendicular to the plane of the layer, an x-ray reflector having an axis, the axis of the x-ray reflector disposed substantially perpendicular to the plane of the layer, the x-ray reflector formed of a single crystal structure of at least one of silicon, germanium, and lithium fluoride, and having a crystal plane bent in a first direction along the axis and in a second direction around the axis, the x-ray reflector adapted for receiving the x-rays from the linear focus x-ray tube and directing the x-rays received to a target spot on the layer at angles whereby the x-rays reflect off of the layer as reflected x-rays at a reflection angle, where the reflected x-rays have properties that are indicative of the characteristics of the layer, a first x-ray blocking barrier disposed substantially perpendicular to the plane of the layer, the first x-ray blocking barrier further disposed above the target spot on the layer, the first x-ray blocking barrier adapted for blocking at least a portion of the x-rays director toward and reflected off of the layer, the first x-ray blocking barrier and the layer defining a gap, where a size of the gap determines at least in part both a throughput and an angular resolution of the x-rays reflected off the layer, where the gap is adjustable through a range, a movable stage adapted to selectively raise and lower the layer relative to the first x-ray blocking barrier, and thereby adjust the size of the gap, a sensor adapted to determine the size of the gap, a second x-ray blocking barrier disposed substantially perpendicular to the plane of the layer, the second x-ray blocking barrier disposed between the x-ray reflector and the layer, the second x-ray blocking barrier adapted for blocking at least a portion of any x-rays that are not directed to the target spot on the layer, a charge coupled device array receptor adapted for receiving the reflected x-rays and producing signals based on the properties of the reflected x-rays, including an intensity of the reflected x-rays as a function of angle of the reflected x-rays, and an analyzer adapted for receiving the signals from the receptor and determining the characteristics of the layer based at least in part on the properties of the reflected x-rays.

* * * * *